United States Patent
Kunita et al.

(10) Patent No.: US 7,334,283 B2
(45) Date of Patent: Feb. 26, 2008

(54) POWER TOOTHBRUSH

(75) Inventors: Tomohiro Kunita, Hikone (JP); Shinichi Taniguchi, Hikone (JP)

(73) Assignee: Matsushita Electric Works, Ltd., Osaka (JP)

( * ) Notice: Subject to any disclaimer, the term of this patent is extended or adjusted under 35 U.S.C. 154(b) by 753 days.

(21) Appl. No.: 10/479,977

(22) PCT Filed: Jun. 11, 2002

(86) PCT No.: PCT/JP02/05764

§ 371 (c)(1),
(2), (4) Date: Dec. 12, 2003

(87) PCT Pub. No.: WO02/102187

PCT Pub. Date: Dec. 27, 2002

(65) Prior Publication Data

US 2004/0168269 A1    Sep. 2, 2004

(30) Foreign Application Priority Data

Jun. 14, 2001   (JP) .............................. 2001-180804
Jan. 18, 2002   (JP) .............................. 2002-010831

(51) Int. Cl.
*A46B 7/08* (2006.01)
*A46B 9/10* (2006.01)

(52) U.S. Cl. .............................. 15/28; 15/29; 15/167.1; 15/201

(58) Field of Classification Search ..................... None
See application file for complete search history.

(56) References Cited

U.S. PATENT DOCUMENTS

| | | | |
|---|---|---|---|
| 2,882,544 A * | 4/1959 | Hadidian | ................... 15/167.1 |
| 3,758,798 A | 9/1973 | Holly | |
| 3,771,189 A * | 11/1973 | Horton et al. | ................. 15/179 |
| 4,694,844 A | 9/1987 | Berl et al. | |
| 5,184,368 A * | 2/1993 | Holland | ..................... 15/167.1 |
| 5,435,032 A * | 7/1995 | McDougall | ................. 15/22.1 |
| 5,524,319 A | 6/1996 | Avidor | |
| 5,715,556 A | 2/1998 | Chung | |
| 6,161,245 A * | 12/2000 | Weihrauch | ................... 15/201 |
| 2001/0001334 A1 * | 5/2001 | Gruber et al. | ............... 15/22.1 |

FOREIGN PATENT DOCUMENTS

| | | |
|---|---|---|
| JP | 5-123218 | 5/1993 |
| JP | 7-265127 | 10/1995 |
| JP | 8-000356 | 1/1996 |

OTHER PUBLICATIONS

English Language Abstract JP 5-123218.
English Language Abstract JP7-265127.
English Language Abstract of JP 8-000356.

* cited by examiner

*Primary Examiner*—David Redding
(74) *Attorney, Agent, or Firm*—Greenblum & Bernstein, P.L.C.

(57) ABSTRACT

In a power toothbrush, a brush base portion is provided at a top end of a brush attachment which is detachably engaged with a main body containing an actuator generating driving force for driving at least the brush base portion. The brush base portion can be reciprocally moved in an axial direction of the main body with a predetermined stroke and a predetermined frequency, swing around a rotation axis perpendicular to the axial direction of the main body with a predetermined swing angle and a predetermined frequency, or rotated around the rotation axis with a predetermined rotation speed. A plurality of floating base member is floatingly supported in guiding hollows formed in the brush base portion, and a brush staple is planted on each floating base member. Thus, dirt or plaque remained in interdental portion of the tooth can effectively be removed, when top ends of the brush staples contact the surfaces of the tooth.

16 Claims, 11 Drawing Sheets

POWER TOOTHBRUSH

TECHNICAL FIELD

The present invention relates to a power toothbrush in which at least a brush base portion of a brush attachment is driven by an actuator with respect to a main body thereof, and especially brush staples are floatingly movable with respect to the brush attachment.

BACKGROUND ART

Figure 13:
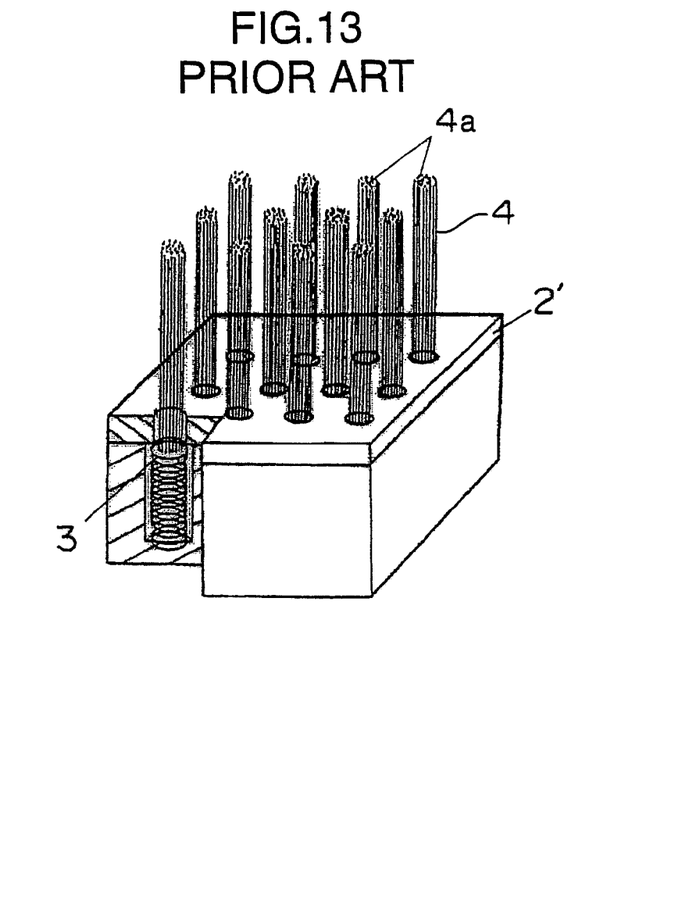
FIG. 13 is a partially sectional perspective view for showing a configuration of a conventional toothbrush.
Figure 14:
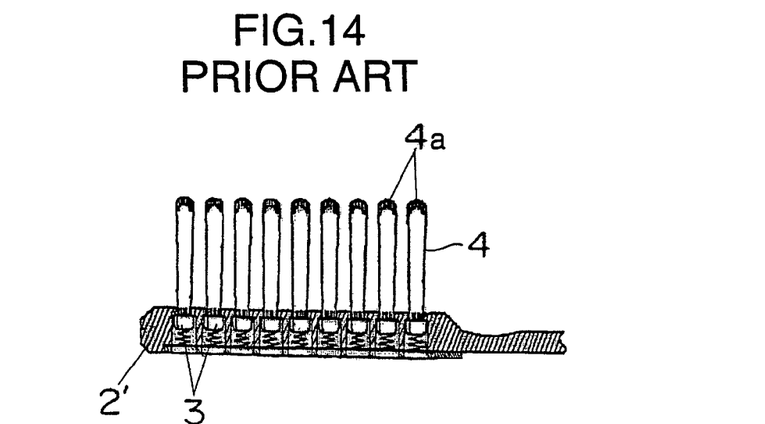
FIG. 14 is a cross-sectional front view for showing a configuration of another conventional toothbrush.

Conventional toothbrushes, in which brush staples are floatingly movable with respect to brush base portion, are described in, for example, Publication Gazette of Japanese Patent Application 5-123218 shown in FIG. 13 and Publication Gazette of Japanese Patent Application 7-265127 shown in FIG. 14. In the conventional toothbrushes which are not the power toothbrush, a brush base portion 2' is formed in the vicinity of a top end opposite to a grip portion of a main body the toothbrush. A plurality of floating bases 3 is floatingly provided in the brush base portion 2', and a blush staple 4 is planted on each floating base 3.

In the conventional toothbrush, the brush staples 4 are floatingly movable with respect to the brush base portion 2', so that top ends 4a of the brush staples 4 can be contacted along convex and concave shapes of human teeth (not shown in the figure). Thus, dirt on the teeth such as plaque and so on can be removed while the teeth are polished.

In the conventional toothbrush in which the brush staples 4 are floatingly movable with respect to the brush base portion 2', the brush base portion 2', however, is integrally formed with the grip portion as the main body of the toothbrush. It is necessary to move the main body of the toothbrush reciprocally or rollingly by human hand for removing the dirt of the tooth. In such the case, the top ends 4a of the brush staples 4 can be contacted along the convex and concave shapes of the human teeth. Stroke and frequency of the reciprocal motion or the rolling motion of the toothbrush, however, become uneven. When the brush staples 4 are moved in the interdental portion of the teeth where much dirt is remained, it is necessary to move the brush staples 4 largely. Thus, the brush staples 4 occasionally polish another teeth faces when the brush staples 4 move over the interdental portion of the teeth, or a part of the brush staple 4 occasionally is hooked on the interdental portion of the teeth. As a result, the conventional toothbrush cannot remove the dirt in the interdental portion of the teeth effectively.

DISCLOSURE OF INVENTION

An objective of the present invention is to provide a power toothbrush for reciprocally moving, swing or rolling at least a brush base portion of a brush attachment with a predetermined stroke or a predetermined rolling angle, and a predetermined frequency, in which the brush staples are floatingly movable in the brush base portion so as to be contacted the convex and concave surfaces of the teeth.

A power toothbrush in accordance with the present invention comprises a main body and a brush attachment detachably engaged with the main body. A brush base portion, which is reciprocally moving in an axial direction of the main body or rolling around an axis perpendicular to the axial direction of the main body, is provided in the vicinity of a top end of the brush attachment. At least a brush staple is planted on each floating base member. A plurality of floating base members is floatingly supported in guiding hollows formed in the brush base portion in a manner so that the top ends of the brush staples are protruded from the guiding hollows.

By such a configuration, when the top ends of the brush staples are contacted on surfaces of the teeth along the convex and concave shapes of the teeth, and the brush base portion is driven by a predetermined stroke or a predetermined swing angle and a predetermined frequency or predetermined rolling speed, the dirt or plaque remained in the interdental portion of the teeth can be removed effectively.

BEST MODE FOR CARRYING OUT THE INVENTION

FIRST EMBODIMENT

A first embodiment of the present invention is described with reference to FIGS. 1, 2, 3A, 3B and 4.

Figure 1:
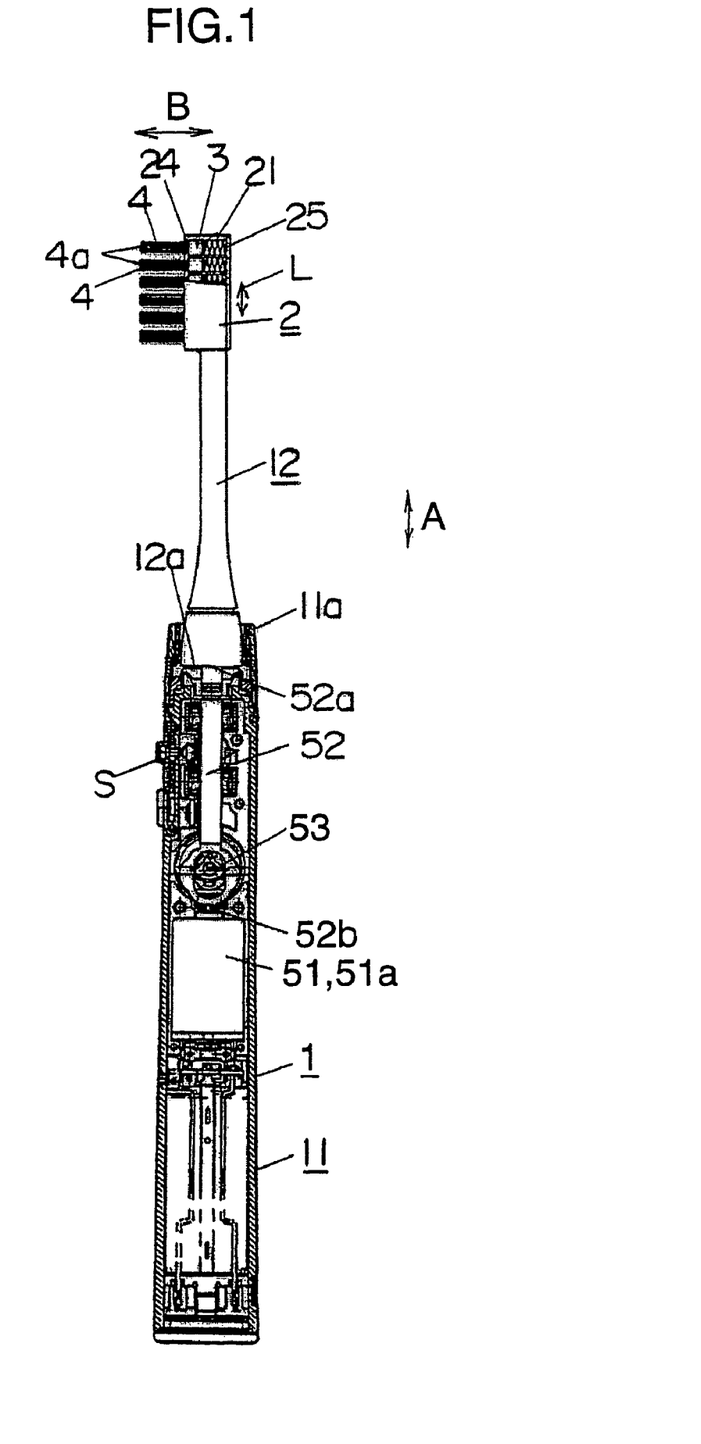
FIG. 1 is a cross-sectional front view for showing an example of a configuration of a power toothbrush in a first embodiment of the present invention.

As can be seen from FIG. 1, a main body 11 having a shank shape and a brush attachment 12 configure a power toothbrush 1. The brush attachment 12 is detachably engaged with the main body 11. A brush base portion 2 is formed at a top end of the brush attachment 12. A plurality of floating base members 3 is floatingly provided in the brush base portion 2 of the brush attachment 12. A brush staple 4 is planted on each floating base member 3. A portion in the vicinity of a bottom end of the main body 11 serves as a grip of the power toothbrush 1.

Figure 2:
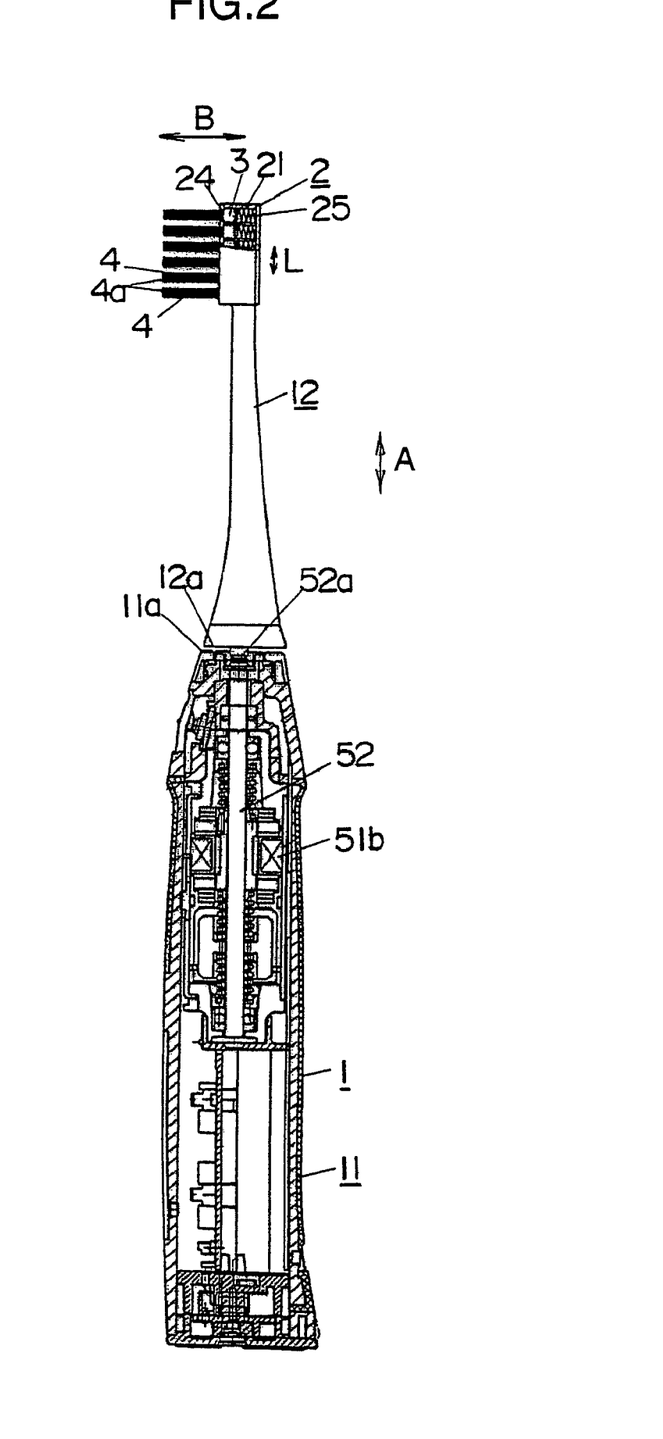
FIG. 2 is a cross-sectional front view for showing another example of the configuration of the power toothbrush in the first embodiment.

An actuator 51 such as an electric motor and the driving shaft 52 for transmitting driving force of the actuator 51 to the brush attachment 12 are provided in the main body 11. A switch "S" whish will be used for switching on and off of the actuator 51 and for selecting the driving state of the actuator 51 is provided on a surface of the main body 11. In the examples shown in FIGS. 1 and 3, a DC motor 51a is used as the actuator 51. It is possible to use another actuator such as a linear oscillator 51b as shown in FIG. 2 as the actuator 51. The kinds of the actuator 51 are not restricted in the present invention.

Figure 3A:
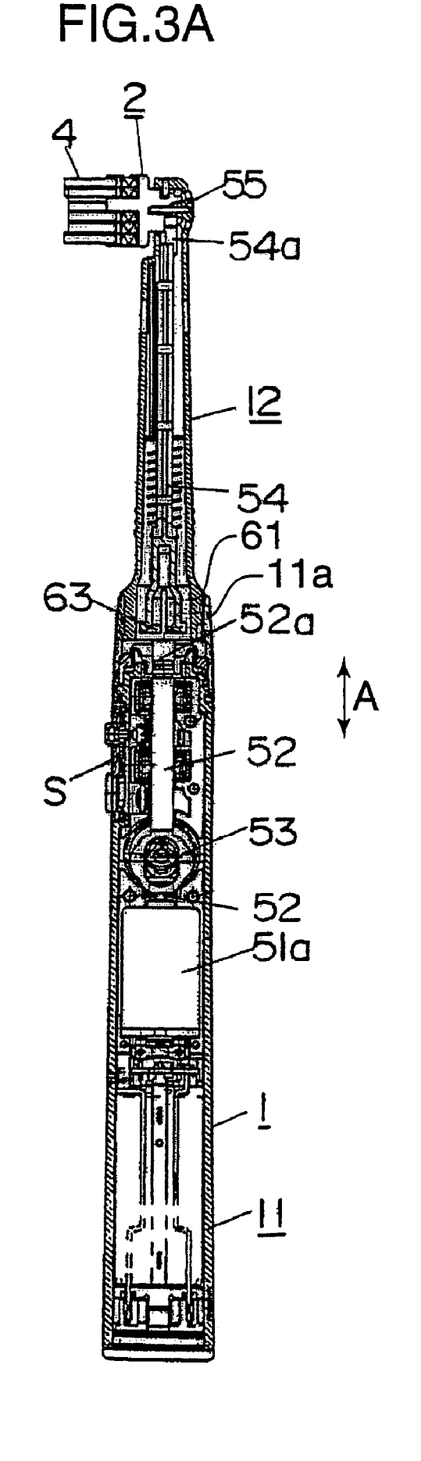
FIG. 3A is a cross-sectional front view for showing still another example of the configuration of the power toothbrush in the first embodiment.
Figure 3B:
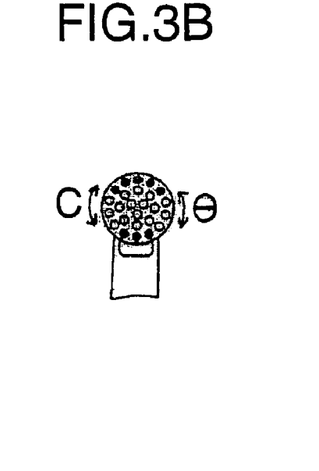
FIG. 3B is a side view for showing an appearance of a brush base portion of the example shown in FIG. 3A.

In the examples shown in FIGS. 1, 3A and 3B, a converter 53 is provided between the actuator 51 (or the DC motor 51a) and the driving shaft 52. The converter 53 is configured by, for example, a cum, a gear, and so on for converting the rotation of a shaft 52b of the DC motor 51a to alternative of the reciprocal motion of the driving shaft 52 in a direction shown by arrow "A" and the swing motion of the driving shaft 52 around the center axis of the shafts 52 and 52b. An end 52a of the driving shaft 52 is protruded from a top end 11a of the main body 11.

In the examples shown in FIGS. 1 and 2, the brush attachment 12 has a slender rod shape except the brush base portion 2. A coupler 12a by which the brush attachment 12 is detachably coupled with the top end 52a of the driving shaft 52 is provided on the bottom end of the brush attachment 12. When the driving shaft 52 is reciprocally moved or swung, the brush attachment 12 is also reciprocally moved or swung corresponding to the reciprocal motion or swing motion of the driving shaft 12, so that the brush base portion 2 of the brush attachment 12 is reciprocally moved or swung.

In the example shown in FIGS. 3A and 3B, an engaging portion 61 formed on the bottom end of the brush attachment 12 is detachably engaged with and fixed on an inside face of the top end 11a of the base member 11. In this example, the brush attachment 12 is not movable except the brush base portion 2. The brush base portion 2 having a disc shape is provided at the top end of the brush attachment 12 in a manner so that the brush base portion 2 is swung around the center axis of the disc shape in the direction shown by arrow "C" as shown in FIG. 3B.

A driving shaft 54 and a brush converter 55 are provided in the brush attachment 12. A coupler 63 coupled with the top end 52a of the driving shaft 52 is formed at a bottom end of the driving shaft 54, so that the driving shaft 54 is swung around the center axis of the driving shaft 54 corresponding to the swing motion of the driving shaft 52. A gear is formed at a top end 54a of the driving shaft 54 that is engaged with a gear portion of the brush converter 55. The brush base portion 2 is detachably fixed on the brush converter 55. The brush converter 55 is, for example, a gear with which the gear at the top end 54a of the driving shaft 54 is engaged, so that the brush converter 55 can convert the swing motion of the driving shaft 54 to the swing motion of the brush base portion 2 in the direction shown by arrow "C".

By such a configuration, when the engaging portion 61 of the brush attachment 12 is engaged with the top end 11a of the main body 11, the coupler 63 of the driving shaft 54 is coupled with the top end 52a of the driving shaft 52. The swinging driving force of the driving shaft 52 is transmitted to the brush converter 55 via the driving shaft 54 and converted to the swing motion of the brush base portion 2 around the center axis thereof perpendicular to the center axis of the driving shafts 52 and 54 by the brush converter 55. The motion of the brush base portion 2 in accordance with the present invention is not restricted by this example. It is possible continuously to rotate the brush base portion 2 in a predetermined direction.

As described above, the brush base portion 2 can be driven with respect to the main body 11 by the driving force of the actuator 51.

Subsequently, the details of the brush base portion 2 with respect to the examples shown in FIGS. 1 and 2 are described. As can be seen from FIG. 4, a plurality of guiding hollows 21 is formed on the brush base portion 2. A floating base member 3 is floatingly supported in each guiding hollow 21.

Figure 4:
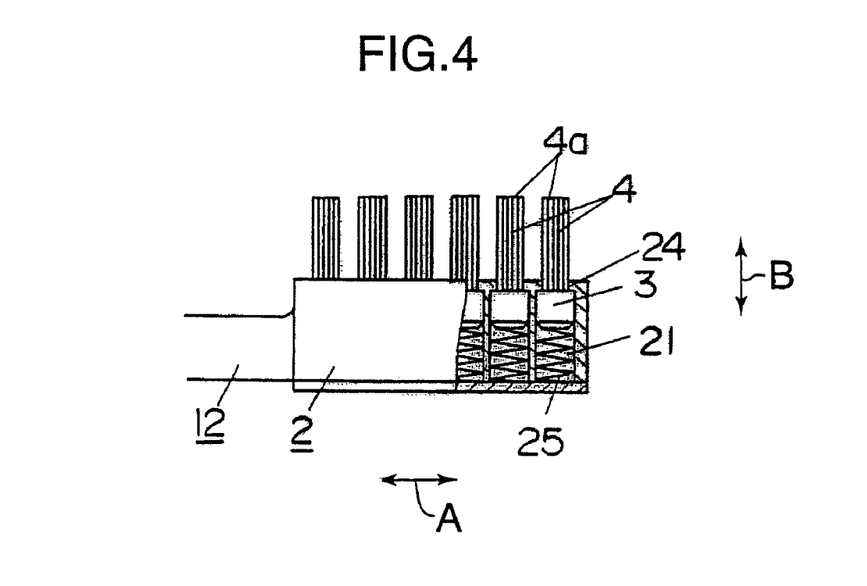
FIG. 4 is a partially sectional front view for showing an example of a detailed configuration of the brush base portion in the first embodiment.

The guiding hollow 21 is a cylindrical hollow having an axis in the direction shown by arrow "B" perpendicular to the axis of the reciprocal motion of the brush attachment 12 shown by arrow "A". A plurality of the guiding hollows 21 is arranged in the brush base portion 2. A through hole 24 having a diameter smaller than that of the guiding hollow 21 is formed on each top wall of the guiding hollow 21. The floating base member 3 is floatingly inserted in the guiding hollow 21.

The floating base member 3 is a cylinder having a diameter substantially the same as but a little smaller than the diameter of the guiding hollow 21 and having a height lower than the height of the guiding hollow 21. In this example, the shapes of the guiding hollow 21 and the floating base member 3 are formed cylindrical, but the shapes of them in the present invention are not restricted by the example. When the floating base member 3 can be engaged with the guiding hollow 21, they can have any shapes.

When the floating base member 3 is inserted in the guiding hollow 21, the floating base member 3 can slide in the guiding hollow 21. A spring 25 is provided between the floating base member 3 and the bottom wall of the guiding hollow 21, so that the floating base member 3 is forced to contact the inside of the top wall of the guiding hollow 21. In this example, a coil spring is used as the spring 25, but the type of the spring 25 in the present invention is not restricted by this example.

A brush staple 4 is planted on each floating base member 3. The floating base member 3 is inserted in the guiding hollow 21 in a manner so that the brush staple 4 protrudes from the through hole 24. In the example shown in FIG. 4, a top end 4a of the brush staple 4 is flat on a plane perpendicular to the direction of the protruding of the brush staple 4. Furthermore, the top ends 4a of every brush staples 4 are formed to be the same level.

When the brush base portion 2 of the brush attachment 12 is inserted into the mouth for polishing the surfaces of the teeth, some brush staples 4 contact the surfaces of the teeth.

The floating bases 3 with the brush staples 4 contacting the surfaces of the teeth are moved backward in the guiding hollows 21 against the pressing force of the spring 25. Alternatively, the floating bases 3 with the brush staples 4 not contacting the surfaces of the teeth will be moved backward in the guiding hollows 21 against the pressing force of the spring 25 when the brush base portion 2 is further moved toward the teeth. Thus, the top ends 4a of the brush staples 4 can easily contact the surfaces of the teeth along the convex and concave shapes of the teeth.

For polishing the teeth by using this power toothbrush 1, the position of the switch is selected to drive the actuator 51 under a predetermined condition so that the brush base portion 2 is reciprocally moved, swung or rotated. When the brush base portion 2 is inserted into the mouth and the top ends 4a of the brush staples 4 contact the surfaces of the teeth to be polished, the polishing of the surfaces of the teeth starts. Since the brush staples 4 are planted on the floating base member 3 which are floatingly supported in the brush base portion 2, the top ends 4a of the brush staples 4 are driven corresponding to the motion of the brush base portion 2 driven with a stroke "L" or vibration angle "θ", and a frequency "f" while the top ends 4a of the brush staples 4 contact along the convex and concave surfaces of the teeth. In case of the power toothbrush shown in FIG. 1 or 2, it is preferable that the brush base portion 2 is reciprocally moved with a stroke "L" in a range between 0.5 mm to 5 mm and a frequency "f" in a range between 20 Hz to 300 Hz. Since the brush staples 4 are reciprocally moved with the stroke "L" in the range between 0.5 mm to 5 mm in the interdental portions of the teeth, the brush staples 4 rarely polishes the portion distant from the interdental portion. Since the frequency "f" of the reciprocal motion is larger than 20 Hz, the brush staples 4 are moved much faster than the motion of human hand. Furthermore, the frequency "f" of the reciprocal motion is larger than 300 Hz, feeling of the tooth polishing will become good.

As mentioned above, the brush base portion 2 is provided in the vicinity of the top end of the brush attachment 12 and the brush staples 4 are planted on the floating base member 3 which is floatingly supported in the brush base portion 2, so that the dirt or plaque on the teeth remained in the interdental portion can be removed effectively by driving the brush base portion 2 with the predetermined stroke "L", the swing angle "θ" and the frequency "f", or rotating the brush base portion 2 with the predetermined rotation speed.

In the above-mentioned examples, the main body 11 and the detachable brush attachment 12 configure the power toothbrush 1. It is possible that portions except the brush base portion 2 of the brush attachment 12 can integrally be provided on the main body 11 and an attachment corresponding to the brush base portion 2 is detachably engaged with the main body 11.

Figure 5:
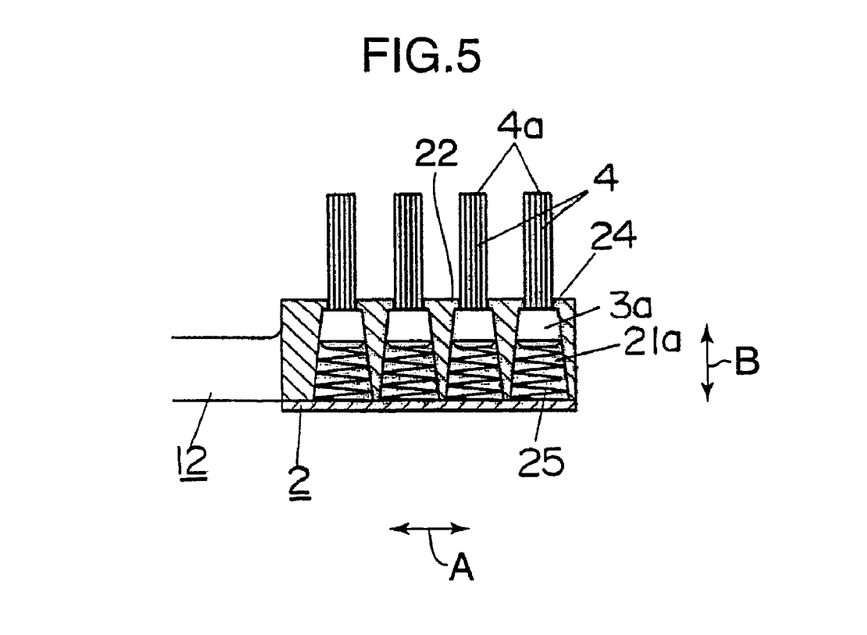
FIG. 5 is a cross-sectional front view for showing another example of the brush base portion in the first embodiment.

Another example shown in FIG. 5 is described. The different points from the above-mentioned examples are mainly explained.

In the example shown in FIG. 5, the guiding hollows 21a with having a circular truncated cone shape are formed on the brush base portion 2, and the floating base members 3a are formed substantially the same shape as a part of the circular truncated cone of the guiding hollows 21a.

The guiding hollow 21a is the circular truncated cone shaped hollow having an axis in the direction shown by arrow "B" perpendicular to the axis of the reciprocal motion of the brush attachment 12 shown by arrow "A". A plurality of the guiding hollows 21a is arranged in the brush base portion 2. A through hole 24 having a diameter smaller than that of the guiding hollow 21a is formed on each top wall 22 having the smallest diameter of the guiding hollow 21a.

The floating base member 3a floatingly supported in the guiding hollow 21a has the circular truncated cone shape with a height about ⅓ of the height of the guiding hollow 21a from the top wall 22 to the bottom wall thereof. When the floating base member 3a is inserted in the guiding hollow 21a and the floating base. member 3a is moved at an upper end in the guiding hollow 21a, the inner face of the guiding hollow 21a tightly contacts the outer face of the floating base member 3a are tightly. The floating base member 3a can be moved in the direction shown by arrow "B". The spring 25 is provided between the floating base member 3a and the bottom wall of the guiding hollow 21a, so that the floating base member 3a is forced toward the top wall 22 of the guiding hollow 21a.

By such a configuration, the floating base member 3a may not be twisted in the guiding hollow 21a, even when a load is applied to the top end 4a of the brush staple 4 in a direction perpendicular to the original planting direction of the brush staple 4 while the teeth are polished.

Figure 6A:
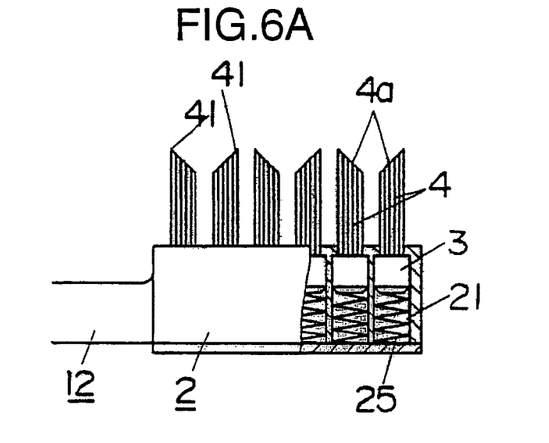
FIGS. 6A to 6C are partially sectional front views for showing still other examples of the brush base portion in the first embodiment.
Figure 6B:
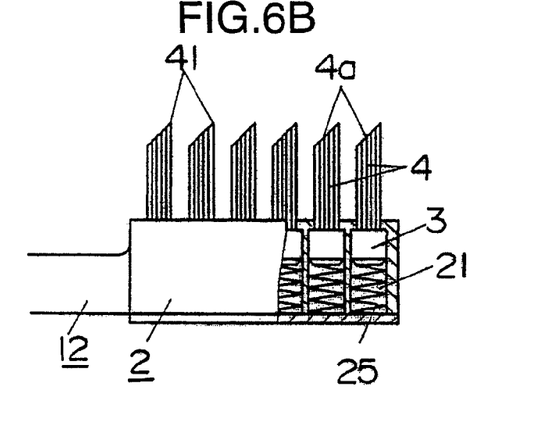
Figure 6C:
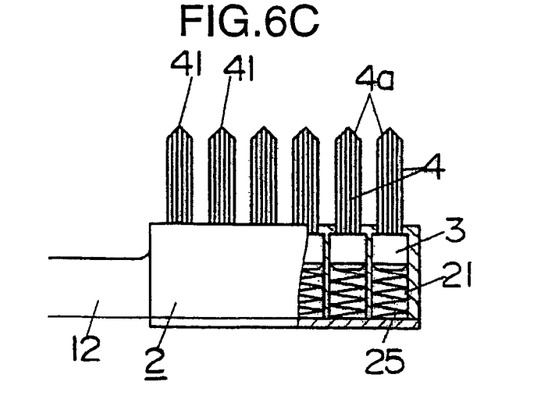

Still other examples shown in FIGS. 6A to 6C are described. In these examples, the top ends 4a of the brush staples 4 are cut to slant for forming the peaks 41. In the example shown in FIG. 6A, the top ends 4a of adjoining two brush staples 4 are cut to slant in the opposite directions. In the example shown in FIG. 6B, the top ends 4a of every brush staples 4 are cut to slant in the same direction. In the example shown in FIG. 6C, the top end 4a of each brush staple 4 is cut to have a chevron shape for forming the peak 41 at the center of the brush staple 4. By such configurations, the top ends 4a of the brush staples 4 can easily and certainly contact the surfaces of the interdental portions of the teeth.

Figure 7A:
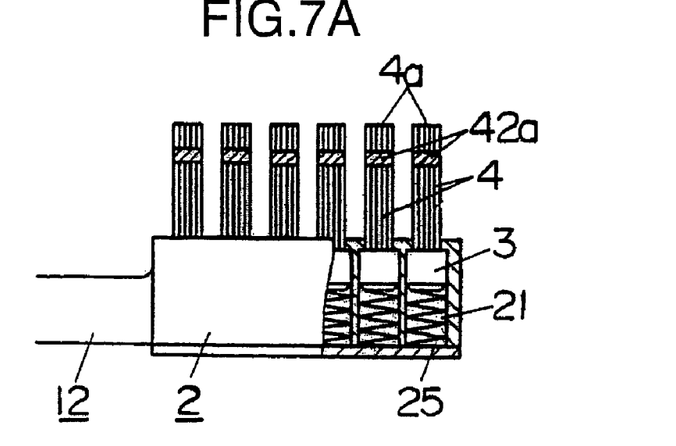
FIGS. 7A to 7C are partially sectional front views for showing still other examples of the brush base portion in the first embodiment.
Figure 7B:
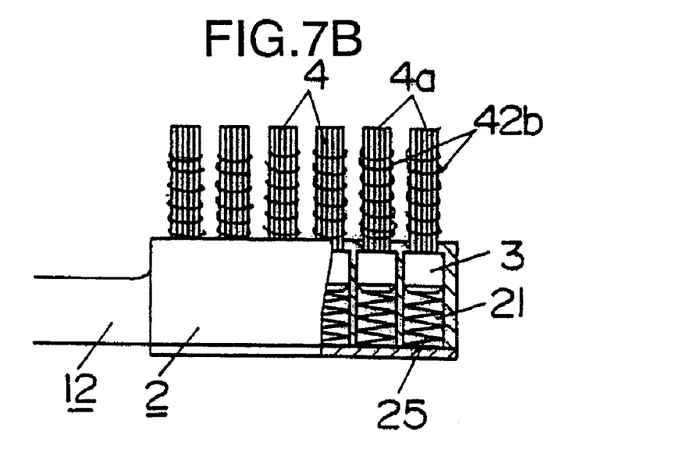
Figure 7C:
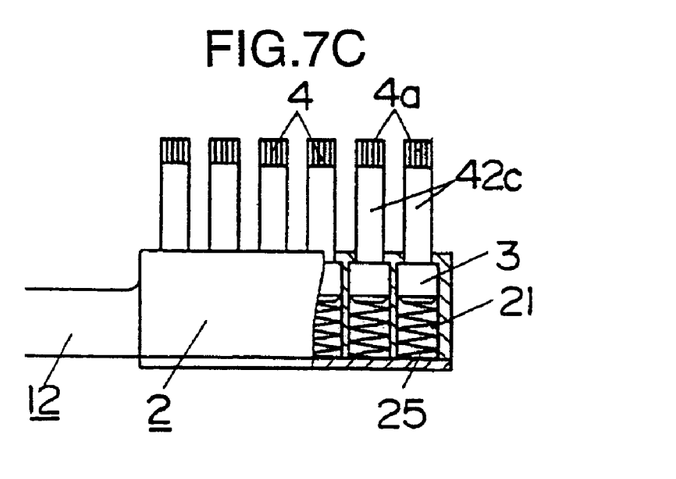
Figure 8A:
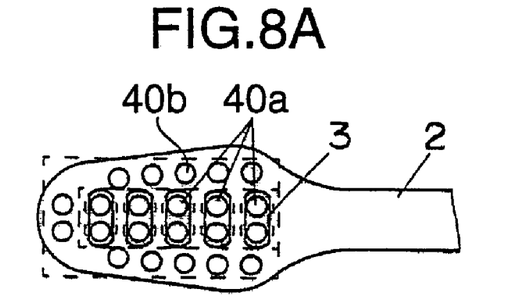
FIG. 8A is a top view of a brush base portion of a power toothbrush in a second embodiment of the present invention.
Figure 8B:
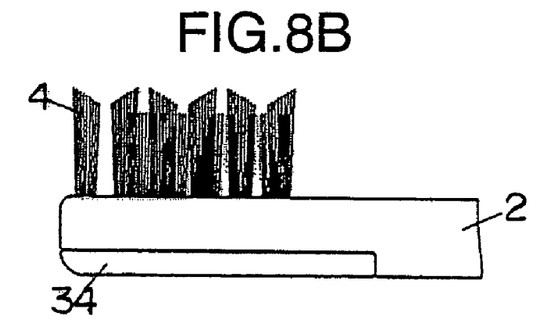
FIG. 8B is a front view of the brush base portion in the second embodiment.
Figure 8C:
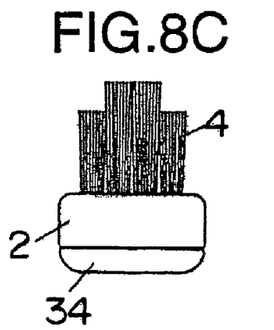
FIG. 8C is a side view of the brush base portion in the second embodiment.
Figure 8D:
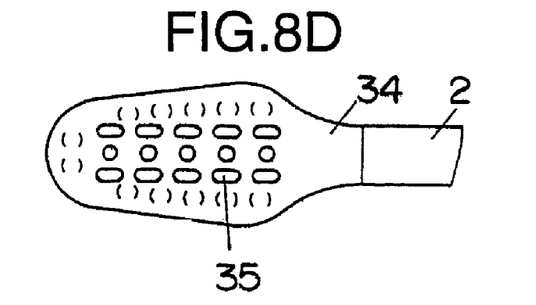
FIG. 8D is a bottom view of the brush base portion in the second embodiment.

Still other examples shown in FIGS. 7A to 7C are described. In these examples, fasteners 42 for preventing the brush staples 4 unfasten are provided except the top ends 4a of the brush staples 4. In the example shown in FIG. 7A, a portion lower about ⅓ of the height of the brush staple 4 from the top end 4a of each brush staple 4 is melted to form a ring shaped fastener 42. In the example shown in FIG. 7B, a coil shaped fastener 42 is wound around each brush staple 4. In the example shown in FIG. 7C, a tube shaped fastener 42 is covered each brush staple 4 from the bottom to a portion lower about ⅓ of the height of the brush staple 4 from the top end 4a of the brush staple 4. By such configurations, it is possible to prevent the brush staple 4 unfasten while the brush attachment 12 is used for polishing the teeth in a long time.

SECOND EMBODIMENT

A second embodiment of the present invention is described with reference to FIGS. 8A to 8D, 9 and 10, 11A to 11C, 12A and 12B.

In comparison with the above-mentioned first embodiment, brush staples 40b are directly planted on the brush base portion 2 of the brush attachment surrounding brush staples 40a planted on the floating base member 3. Two brush staples 40a are planted on each floating base member 3, and each floating base member 3 is floatingly supported by a single spring 25. The brush staples 40a are fitted into planting holes 30 formed on the floating base member 3. Both sides of the floating base members 3 are tapered, while the sidewalls of the guiding hollows 21 are not tapered. A boss 32, with which the top end of the spring 25 such as a coil spring is engaged, is formed on the bottom face of the floating base member 3. A spot facing 27, to which the bottom end of the spring 25 is inserted, is formed on the bottom face 26 of the guiding hollow 21.

In the second embodiment, the brush staples 40b, which are directly planted on the brush base portion 2, are independently provided for surrounding the brush staples 40a planted on the floating base members 3. As shown in FIG. 8, a plurality of, for example, five floating base members 3 with the brush staples 40a are provided at the center portion of the brush base portion 2. The brush staples 40b are directly planted on the brush base portion 2 for surrounding the brush staples 40a planted on the floating base members 3. By such a configuration, an area of the brush base portion 2 in which the brush staples 40a and 40b are planted can be made smaller. A thickness of the brush base portion 2 becomes about 5 mm to 6 mm, but the edges of the brush base portion 2 can be made round having a radius larger than 1 mm, so that the user feels the edge of the brush base portion 2 not so much as discomfort, and the brushing of the power toothbrush 1 becomes safety.

Since two brush staples 40a are planted on one floating base member 3 and each floating base member 3 is floatingly supported by one spring 25 in the brush base portion 2, the workability for assembling the spring 25 and the floating base member 3 with the brush staples 4 in the brush base portion 2 can be increased and the manufacturing cost of the brush attachment can be reduced.

Figure 9:
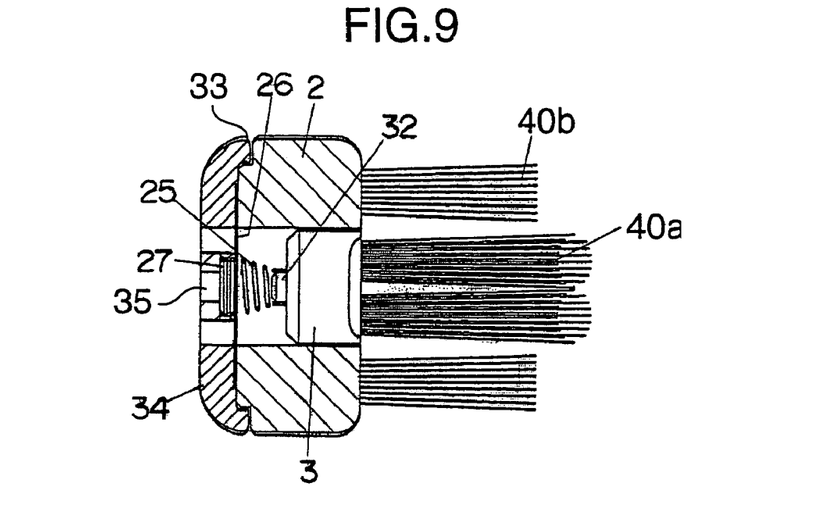
FIG. 9 is a cross-sectional side view for showing a configuration of the brush base portion in the second embodiment.
Figure 10:
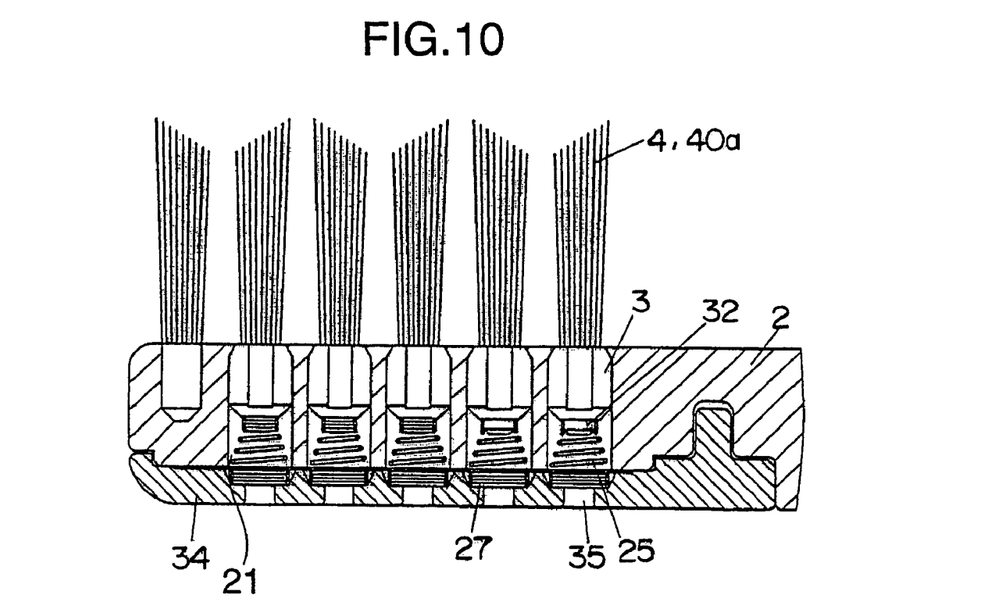
FIG. 10 is a cross-sectional front view for showing the configuration of the brush base portion in the second embodiment.
Figure 11A:
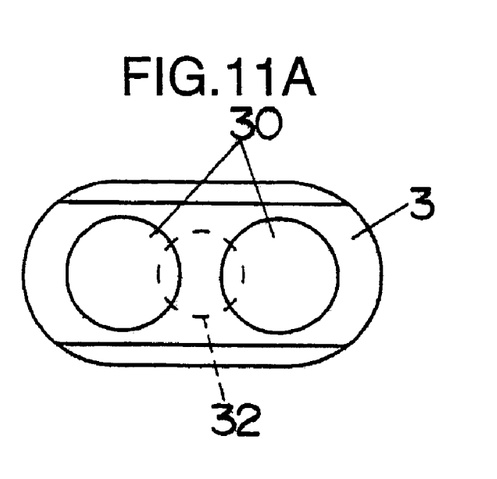
FIG. 11A is a top view of a floating base member in the second embodiment.
Figure 11B:
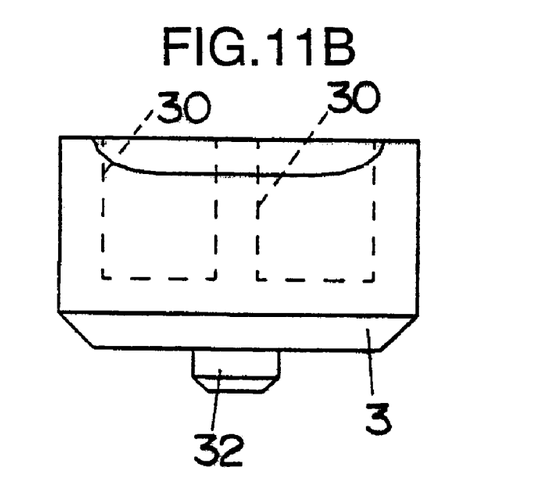
FIG. 11B is a side view of the floating base member in the second embodiment.
Figure 11C:
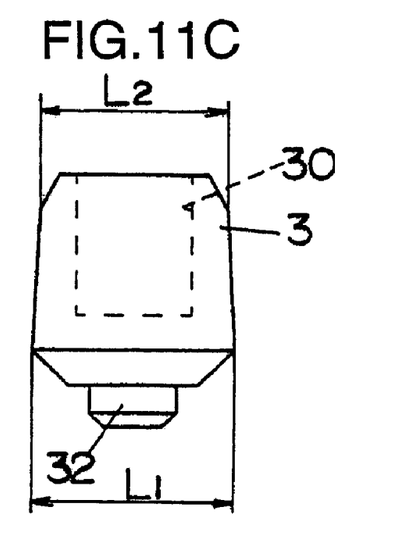
FIG. 11C is a front view of the floating base member in the second embodiment.

As shown in FIGS. 9 and 10, the boss 32, to which the top end of the spring 25 is engaged, is formed on the bottom face of the floating base member 32. The spot facing 27, to which the bottom end of the spring 25 is inserted, is formed on the bottom face 26 of the guiding hollow 21. The floating base members 3 are respectively supported by the springs 25 in the brush base portion 2.

An offset portion 33, to which a cover member 34 is fitted, is formed on a rear face of a main portion of the brush base portion 2. Before fitting the cover member 34, the floating base members 3 can be inserted into the guiding hollows 21. After inserting the floating base members 3 into the guiding hollows 21, the top ends of the springs 25 having the smallest diameter are respectively engaged with the bosses 32 formed on the bottom faces of the floating base members 3. The spot facings 27 are formed on the bottom face 26 of the cover member 34 at positions corresponding to the guiding hollows 21. Furthermore, draining holes 35 having a diameter smaller than the diameter of the spring 25 at the bottom end are formed at the center of the spot facings 27 so as to drain the water immerging into the guiding hollows 21.

By such a configuration, the springs 25 are held between the bosses 32 on the bottom face of the floating base members 3 and the spot facings 27 on the cover member 34, when the cover member 34 is fitted to the offset portion 33. The springs 25 are always held at predetermined fixed positions, so that the springs 25 rarely dislocate the position thereof by the impact force, even when the power toothbrush 1 is fallen. Thus, it is possible to maintain the floating of the floating base member 3 with the brush staples 40a.

Figure 12A:
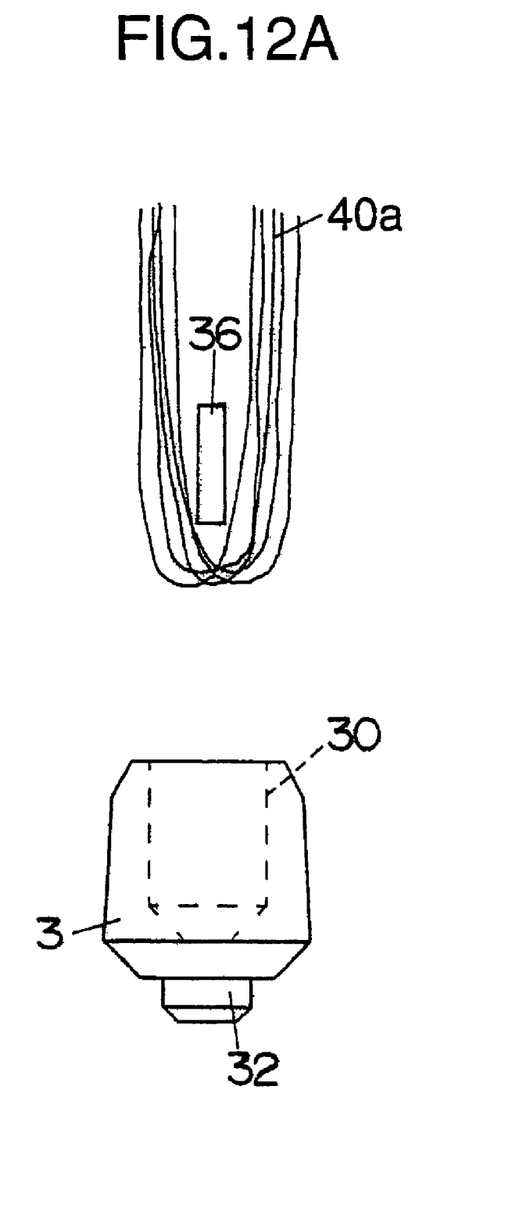
FIGS. 12A and 12B are front views foe showing a planting process of q brush staple on the floating base member in the second embodiment.
Figure 12B:
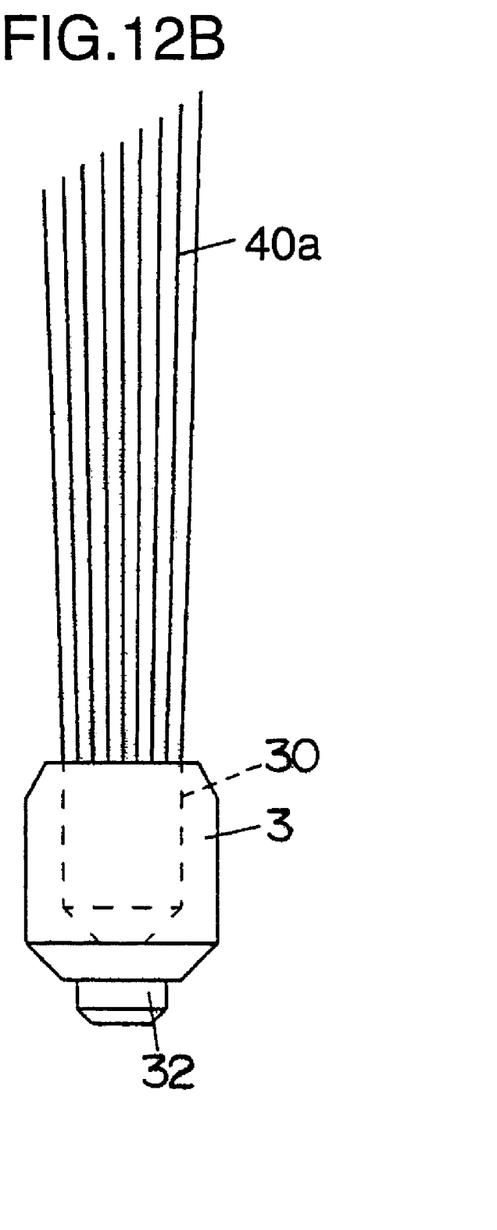

As shown in FIGS. 11A to 11C, 12A and 12B, the floating base member 3 has two planting holes 30 on a top face thereof, to which the brush staples 40a are planted. Both sides of the floating base members 3 are tapered in a manner so that the width $L_2$ at the top end is smaller than the width $L_1$ at the bottom end. As shown in FIG. 12A, each brush staple 40a is planted in a manner so that the brush staple 40a is bent at the center thereof and a fixing member 36 is contacted to the bending point. Subsequently, the fixing member 36 and the brush staple 40a are forcibly embedded into the planting hole 30.

By such a configuration even when the width of upper half portion of the floating base member 3 becomes wider owing to the planting of the brush staples 4 into the planting holes 30, the width of the floating base member 3 can be restricted to be smaller than the width of the guiding hollow 21. Thus, it is possible to prevent the wearing or friction due to the contact of the floating base member 3 on the sidewalls of the guiding hollow 21.

INDUSTRIAL APPLICABILITY

As mentioned above, the power toothbrush in accordance with the present invention comprises a main body and a brush attachment detachably engaged with the main body. The main body includes an actuator for generating a driving force and a driving shaft for transmitting the driving force to the brush attachment. At least two kinds of brush attachment are prepared, so that the user can select one brush attachment suitable for his taste. A brush base portion, which can reciprocally move in an axial direction of the main body, swing or roll around an axis perpendicular to the axial direction of the main body, is formed in the vicinity of a top end of the brush attachment. A plurality of floating base member is floatingly provided in the brush base portion, and at least a brush staple is planted on each floating base member. Thus, when top ends of the brush staples can contact the surfaces of the teeth along the convex and concave shapes of the teeth. Since the brush base portion is driven by a predetermined stroke, a predetermined swing angle and a predetermined frequency or predetermined rotation speed, the dirt or plaque remained in the interdental portion of the teeth can be removed effectively.

Furthermore, it is preferable that the brush base portion is reciprocally moved with a stroke in a range between 0.5 mm to 5 mm. Since the brush staples are reciprocally moved with the stroke in the range between 0.5 mm to 5 mm in the interdental portions of the tooth, the brush staples rarely polishes the portion distant from the interdental portion.

Still furthermore, it is preferable that the brush base portion is reciprocally moved with a frequency in a range between 20 Hz to 300 Hz. Since the frequency of the vibration or the reciprocal movement is larger than 20 Hz, the brush staples are moved much faster than the movement by human hand. Furthermore, since the frequency of the vibration or the reciprocal movement is larger than 300 Hz, feeling of the tooth polishing will become good.

Still furthermore, it is preferable that a plurality of guiding hollows having a circular truncated cone shape is formed in the brush base portion. A through hole having a diameter smaller than that of the guiding hollow is formed on each top wall having the smallest diameter of the guiding hollow. The floating base members formed substantially the same shape as a part of the circular truncated cone of the guiding hollows are freely movable in the guiding hollows in a manner so that the brush staples protrude from the through holes. A spring is provided between the floating base member and the bottom wall of the guiding hollow so that the floating base member is forced toward the top wall of the guiding hollow. Thus, the floating base member may not be twisted in the guiding hollow, even when a load is applied to the top end of the brush staple in a direction perpendicular to the original planting direction of the brush staple while the teeth are polished.

Still furthermore, it is preferable that the top ends of the brush staples are cut to slant for forming the peaks. Thus, the top ends of the brush staples can easily and certainly contact the surfaces of the interdental portions of the teeth.

Still furthermore, it is preferable that a fastener for preventing the brush staple unfasten is provided on each brush staple except a portion in the vicinity of the top end of the brush staple. Thus, it is possible to prevent the brush staple unfasten while the power toothbrush is used for polishing the teeth in a long time.

Still furthermore, it is preferable that brush staples are directly planted on the brush base portion surrounding the brush staples planted on the floating base member. Thus, an area of the brush base portion in which the brush staples are planted can be made smaller. Furthermore, the edges of the brush base portion can be made round having a radius larger than 1 mm, so that the user feels the edge of the brush base portion not so much as discomfort, and the brushing of the power toothbrush 1 becomes safety.

Still furthermore, it is preferable that at least two brush staples are planted on one floating base member and each floating base member is floatingly supported by one spring in the brush base portion. Thus, the workability for assembling the spring and the floating base member with the brush staples in the brush base portion can be increased and the manufacturing cost of the brush attachment can be reduced.

Still furthermore, it is preferable that the floating base member has at least two planting holes to which the brush staples are planted on a top face thereof, and both sides of the floating base members are tapered in a manner so that the width at the top end is smaller than the width at the bottom end. Thus, even when the width of upper half portion of the floating base member becomes wider owing to the planting of the brush staples into the planting holes, the width of the floating base member can be restricted smaller than the width of the guiding hollow. It is possible to prevent the wearing or friction due to the contact of the floating base member on the side face of the guiding hollow.

Still furthermore, it is preferable that an offset portion, to which a cover member is fitted, is formed on a rear face of a main portion of the brush base portion. A boss, with which the top end of the spring is engaged, is formed on a bottom face of the floating base member. A spot facing, to which a bottom end of the spring is inserted, is formed on a face of the cover member facing the guiding hollow. Thus, the springs are fixed between the bosses on the bottom faces of the floating base members and the spot facings on the cover member, when the cover member is fitted to the offset portion. The springs are always held at predetermined fixed positions, so that the springs rarely dislocate the position thereof by the impact force even when the power toothbrush is fallen. It is possible to maintain the floating of the floating base member with the brush staples.

The invention claimed is:

1. A power toothbrush comprising:
    a main body;
    a brush attachment detachably coupled to the main body;
    a brush base portion provided in the vicinity of a distal end of the brush attachment, the brush base portion being configured to reciprocally move in an axial direction of the main body, and to swing or roll around an axis perpendicular to the axial direction of the main body;
    a plurality of floating base members floatingly provided in the brush base portion, each floating base member being provided with at least a brush staple;
    a plurality of guide holes having circular truncated cone-shaped inner surfaces within the brush base portion, the plurality of guide holes having a first generally planar surface provided at a smaller diameter of the truncated cone-shaped inner surfaces and a second generally planar surface provided at a larger diameter of the truncated cone-shaped inner surfaces;
    a plurality of through holes corresponding to the plurality of guide holes, the plurality of through holes being provided in the first generally planar surface and having a diameter smaller than the smaller diameter of the truncated cone-shaped inner surface;
    each floating base member having a shape generally the same as at least a part of a corresponding circular truncated cone-shaped inner surface in which the corresponding floating base member is received, each floating base member being configured to move within the corresponding circular truncated cone-shaped inner surface, and the floating base members having brush staples protruding from corresponding through holes; and
    corresponding springs positioned between corresponding floating base members and the second planar surface of the guide holes, the corresponding springs urging the corresponding floating base members towards the first planar surface.

2. The power toothbrush in accordance with claim 1, wherein the brush base portion is reciprocally moved with a stroke in a range between 0.5 mm to 5 mm.

3. The power toothbrush in accordance with claim 2, wherein the brush base portion is reciprocally moved with a frequency in a range between 20 Hz to 300 Hz.

4. The power toothbrush in accordance with claim 1, wherein the top end of each brush staple is cut at a slant to provide a peak.

5. The power toothbrush in accordance with claim 4, wherein a fastener preventing the brush staple from unfastening is provided on each brush staple at an end received within a corresponding guide hole.

6. The power toothbrush in accordance with claim 5, wherein said brush staples are connected to corresponding floating base members.

7. The power toothbrush in accordance with claim 6, wherein at least two brush staples are connected to one floating base member; and each floating base member is floatingly supported by one spring positioned within the brush base portion.

8. The power toothbrush in accordance with claim 7, wherein the floating base member has at least two receiving holes on a top face which receives the corresponding brush staples, and sides of each floating base member are tapered so that a width at a top end is smaller than a width at a bottom end.

9. The power toothbrush in accordance with claim 8, wherein a boss with which a top end of the spring is engaged is provided on a bottom face of each floating base member, and a spot facing to which a bottom end of the spring is inserted is positioned facing the boss on a bottom face of the guide hole.

10. The power toothbrush in accordance with claim 1, wherein the brush base portion is reciprocally moved with a frequency in a range between of 20 Hz to 300 Hz.

11. The power toothbrush in accordance with claim 1, wherein the top end of each brush staple is cut at a slant to provide a peak.

12. The power toothbrush in accordance with claim 1, wherein a fastener preventing the brush staple from unfastening is provided on each of the brush staples at an end received within a corresponding guide hole.

13. The power toothbrush in accordance with claim 1, wherein brush staples are connected to corresponding floating base members.

14. The power toothbrush in accordance with claim 11, wherein at least two brush staples are connected to one floating base member; and each floating base member is floatingly supported by one spring positioned within the brush base portion.

15. The power toothbrush in accordance with claim 1, wherein the floating base member has at least two planting receiving holes on a top face which receives the corresponding brush staples, and sides of each floating base member are tapered so that a width at a top end is smaller than a width at a bottom end.

16. The power toothbrush in accordance with claim 1, wherein a boss with which a top end of the spring is engaged is provided on a bottom face of each floating base member, and a spot facing to which a bottom end of the spring is inserted is positioned facing the boss on a bottom face of the receiving holes.

* * * * *

UNITED STATES PATENT AND TRADEMARK OFFICE
CERTIFICATE OF CORRECTION

PATENT NO. : 7,334,283 B2 Page 1 of 1
APPLICATION NO. : 10/479977
DATED : February 26, 2008
INVENTOR(S) : Kunita et al.

It is certified that error appears in the above-identified patent and that said Letters Patent is hereby corrected as shown below:

At Column 11, line 6 (Claim 14, line 1) "11" should be --1--.

At Column 11, line 12 (Claim 15, line 2) "planting" should be deleted.

Signed and Sealed this

Seventh Day of October, 2008

JON W. DUDAS
*Director of the United States Patent and Trademark Office*